United States Patent [19]

Merry

[11] 4,266,557
[45] May 12, 1981

[54] LOW FRICTION SYRINGE

[75] Inventor: Jack D. Merry, Sleepy Hollow, Ill.

[73] Assignee: The Kendall Company, Boston, Mass.

[21] Appl. No.: 53,492

[22] Filed: Jun. 29, 1979

Related U.S. Application Data

[63] Continuation of Ser. No. 869,729, Jan. 16, 1978, abandoned.

[51] Int. Cl.³ .............................................. A61B 5/14
[52] U.S. Cl. ................................. 128/763; 128/218 P
[58] Field of Search ......... 128/218 P, 218 PA, 218 R, 128/234, 760, 763, 276

[56] References Cited

FOREIGN PATENT DOCUMENTS

| 2025379 | 12/1971 | Fed. Rep. of Germany | 128/218 P |
| 2514412 | 10/1976 | Fed. Rep. of Germany | 128/218 P |
| 1333235 | 6/1963 | France | 128/218 P |
| 1500009 | 9/1967 | France | 128/218 P |
| 202402 | 3/1966 | Sweden | 128/218 P |

Primary Examiner—John D. Yasko
Attorney, Agent, or Firm—Powell L. Sprunger

[57] ABSTRACT

A low friction syringe comprising, a barrel defining a chamber, a plunger having a distal end received in the barrel chamber, and a plug of elastic material having a body portion secured to the distal end of the plunger. The plug has first and second annular flanges respectively extending forwardly and rearwardly from the body portion. The first and second flanges have an enlarged outer annular lip lightly contacting an inner surface of the barrel, and an annular hinge portion adjacent the body portion to permit flexation of the flanges responsive to differential pressures between a cavity intermediate the flanges and either the chamber or the atmosphere. The flanges also permit free movement of the plug in the chamber under relatively low friction between the plug and the syringe barrel.

3 Claims, 5 Drawing Figures

LOW FRICTION SYRINGE

This is a continuation of application Ser. No. 869,729 filed Jan. 16, 1978, now abandoned.

BACKGROUND OF THE INVENTION

The present invention relates to syringes, and more particularly to syringes which are useful for certain medical procedures.

In recent years, gas analysis of arterial blood has become one of the most important laboratory tests in the management of patients with respiratory and metabolic disorders. However, the collection of a satisfactory arterial blood sample from a patient for analysis has posed a number of difficulties. Initially, in some patients it may be somewhat difficult to ascertain whether the collection device has received arterial or venous blood without measuring for the relatively high arterial pressures during collection. Second, the collection device should minimize contact of the blood sample with air since the air may affect the results of gas analysis. It is also desirable that the sample should not be collected in the presence of a vacuum, since it is believed that the vacuum may modify the gas characteristics of the sample. Finally, the device must prevent coagulation of the blood sample, and should be in a suitable form to permit closure of the sample to air and chilling during the period of time between collection and analysis.

In the past, plastic and ground glass syringes with a needle have been commonly used to collect the samples. However, prior syringes with rubber plugs of conventional design have proven deficient for such purposes due to the relatively high resistance between the syringe plunger and barrel. The plunger resistance in conventional plastic syringes prevents movement of the plunger responsive to arterial pressure alone, and requires that the plunger be manually withdrawn, thus creating an undesirable vacuum in the syringe chamber during collection. Further, since the plungers of such plastic syringes are not sufficiently mobile to move under arterial pressure, they do not provide an indication whether arterial or venous blood is being collected. Although the plungers of the ground glass syringes may be used to detect arterial pressure, the ground glass syringes are excessively expensive relative the plastic syringes.

During other medical procedures, such as an epidural anesthesia procedure, it is necessary to position the tip of a needle at a relatively precise position inside the patient's body. During this particular procedure, the needle tip should be located in the potential epidural space where the body pressure during insertion of the needle is normally slightly negative. If the needle tip has been advanced too far into the body, it projects through the dura mater into the subarachnoid space where the body pressure is positive. A ground glass syringe may be utilized in this procedure to determine the location of the needle tip through use of the relative body pressures, but conventional plastic syringes have not been sufficiently responsive to pressures for this purpose. Since syringes are normally considered a disposable item, it is desirable to reduce their cost to the hospital and patient below that of the relatively expensive ground glass syringes.

SUMMARY OF THE INVENTION

A principal feature of the present invention is the provision of an improved syringe of simplified construction and reduced cost.

The syringe of the present invention comprises, a barrel having an inner surface defining a chamber, a plunger having a distal end received in the barrel chamber, and a plug of elastic material received in the chamber and having a body portion secured to the distal end of the plunger. The plug has a first annular flange extending forwardly from the body portion, with the first flange having an enlarged outer annular lip lightly contacting the inner surface of the barrel, and an annular hinge portion adjacent the body portion of reduced thickness relative the thickness of the lip. The plug has a second annular flange extending rearwardly from the body portion, with the second flange having an enlarged outer annular lip lightly contacting the inner surface of the barrel, and an annular hinge portion adjacent the body portion of reduced thickness relative the thickness of the second flange lip, with the first and second flanges defining an annular cavity intermediate the body portion and the barrel.

A feature of the present invention is that the plug flanges have minimal resistance for the syringe barrel to permit relatively free movement of the plug and plunger in the barrel.

Another feature of the invention is that the first flange flexes against the inner surface of the barrel responsive to a slightly greater pressure in the chamber relative the cavity during forward movement of the plunger in the barrel.

Thus, a feature of the invention is that a seal is accomplished in the syringe while pumping fluid out of the chamber.

Yet another feature of the invention is that the first flange flexes about its hinge away from the inner surface of the barrel responsive to a slightly less pressure in the chamber relative the cavity, and the second flange flexes against the inner surface of the barrel responsive to a slightly less pressure in the communicating chamber and cavity relative atmospheric pressure during rearward movement of the plunger in the barrel.

Accordingly, still another feature of the invention is that a seal is accomplished through cooperation of the first and second flanges during aspiration by the syringe.

A further feature of the invention is that the syringe may be constructed at a reduced cost while providing minimal friction of plunger movement normally accomplished by relatively expensive precision ground glass syringes.

Further features will become more fully apparent in the following description of the embodiments of this invention and from the appended claims.

DESCRIPTION OF THE PREFERRED EMBODIMENTS

Figure 1:
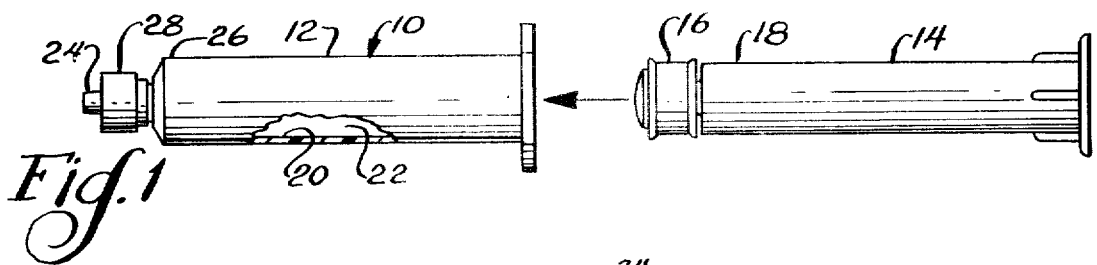
FIG. 1 is an elevational view, partly broken away, of a low friction syringe of the present invention.
Figure 2:
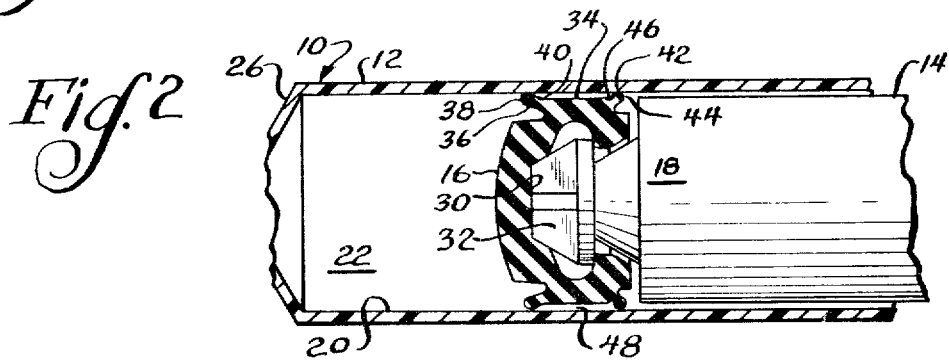
FIG. 2 is a fragmentary sectional view of the syringe of FIG. 1.

Referring now to FIGS. 1 and 2, there is shown a syringe generally designated 10 having a barrel 12, an elongated plunger 14, and a plug 16 of elastic material secured to a distal end 18 of the plunger 14. The syringe barrel 12 has an inner surface 20 defining a chamber 22, a tip 24 at a distal end 26 of the barrel, and a conventional leur lock 28 for securement of the syringe barrel to a suitable instrument, such as a needle (not shown).

With reference to FIG. 2, the plug 16 is slidably received in the barrel chamber 22, and has a main body portion 34 defining a recess 30 which receives a boss 32 projecting forwardly from the distal end 18 of the plunger 14 in order to secure the plug 16 onto the distal end 18 of the plunger. The plug 16 has a first annular flange 36 extending forwardly or distally from the body portion 34 in the syringe chamber, with the first flange 36 having an enlarged outer annular lip 38 which lightly contacts the inner surface 20 of the syringe barrel 12, and an annular hinge portion 40 adjacent the body portion 34 and having a reduced thickness relative the thickness of the lip 38. The plug 16 also has a second annular flange 42 extending rearwardly or proximally from the body portion 34, with the second flange 42 having an enlarged outer annular lip 44 lightly contacting the inner surface 20 of the syringe barrel 12, and an annular hinge portion 46 of reduced thickness relative the thickness of the second flange lip 44. As shown, the first and second flanges 36 and 42 define an annular cavity 48 intermediate the body portion 34 and the inner surface 20 of the barrel 12.

The hinge portions 40 and 46 of the first and second flanges 36 and 42, respectively, permit ready flexation of the flanges relative the barrel 12, and under normal conditions cause slight contact of the respective flange lips 38 and 44 against the syringe barrel 12. As a result, the syringe plug has relatively low friction against movement in the barrel surface 20, permitting free movement of the plunger and plug in the syringe barrel. Thus, the syringe of the present invention may be utilized in special medical procedures, such as collecting arterial blood or an epidural anesthesia procedure, where free movement of the syringe plunger in the barrel is required, previously accomplished by precision ground glass syringes. The syringe barrel 12 and plunger 14 may be made from relatively inexpensive plastic materials, such as polypropylene, while the syringe plug 16 may be constructed from inexpensive elastomers, such as polyisoprene rubber. Thus, the syringe of the present invention may be constructed in a simplified manner from inexpensive parts, while accomplishing results of relatively expensive ground glass syringes.

Figure 3:
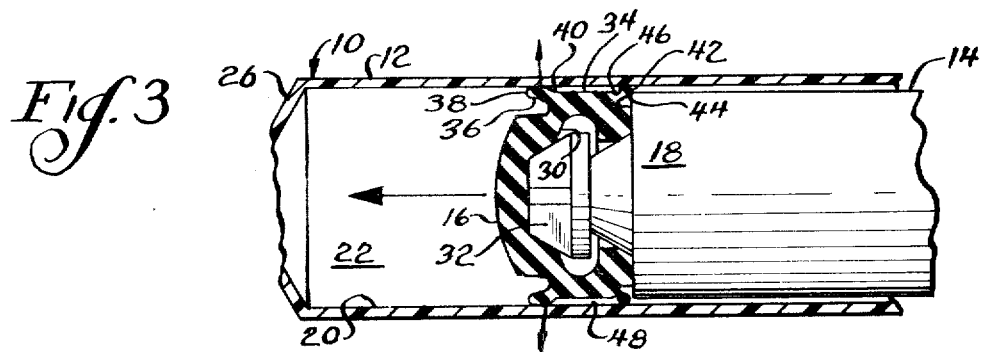
FIG. 3 is a fragmentary sectional view illustrating use of the syringe during forward movement of a syringe plunger and plug in a chamber of the syringe.

In addition to accomplishing this objective, the syringe plug 16 provides an effective seal for pumping and aspirating fluids. With reference to FIG. 3, during forward pumping movement of the syringe plunger 14 in the barrel 12, the pressure in the syringe chamber 22 increases to an amount slightly greater than the pressure in the cavity 48, causing a differential pressure between the chamber 22 and cavity 48 and flexation of the first flange 36 into increased engagement against the inner surface 20 of the syringe barrel 12. As a result, the first flange 36 provides an effective seal for the plug 16 during pumping of fluids from the syringe chamber.

Figure 4:
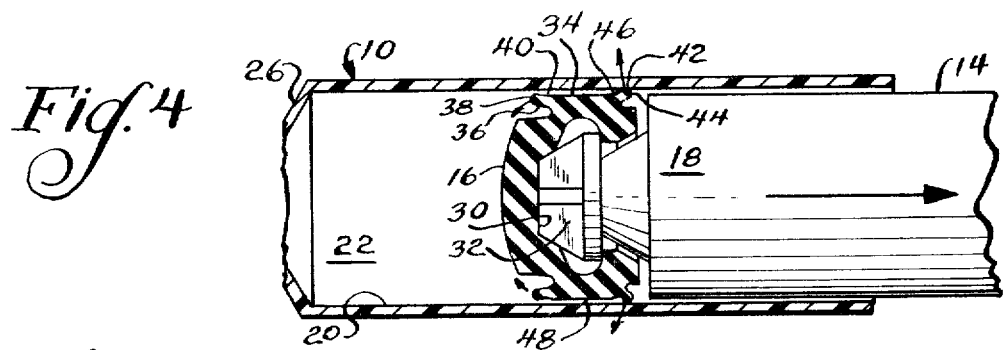
FIG. 4 is a fragmentary sectional view illustrating use of the syringe during rearward movement of the syringe plunger and plug in the chamber.

With reference to FIG. 4, when the syringe plunger is withdrawn slightly in a rearward direction in the chamber 22, during aspiration of fluids, the pressure in the chamber 22 decreases to an amount slightly less than the pressure in the cavity 48, causing inward flexation of the first flange 36 and lip 38 away from the inner surface 20 of the barrel 12 in order to establish communication between the chamber 22 and cavity 48. In this configuration, the pressures in both the communicating chamber 22 and cavity 48 become less than atmospheric pressure outside the plug 16, and the second flange 42 thus flexes against the inner surface 20 of the syringe barrel 12 into increased engagement to accomplish an effective seal during withdrawal of the syringe plunger 14. In this manner, the plug 16 permits aspiration of fluids into the syringe chamber 22.

Thus, in accordance with the present invention, the syringe provides relatively free movement of the plunger and plug along the syringe barrel under conditions of relatively low friction between the plug and barrel in order to permit use of the syringe in special medical procedures, as previously described. Further, the syringe of the invention permits pumping and aspiration of fluids through flexation and cooperation of the plug flanges.

Figure 5:
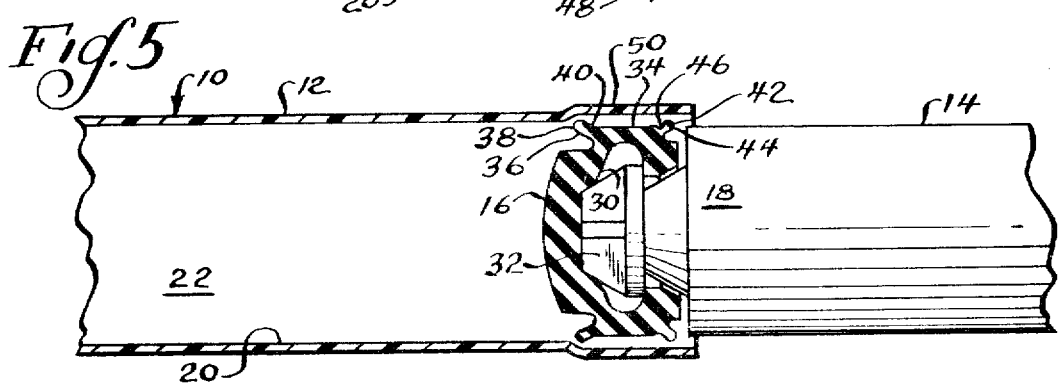
FIG. 5 is an elevational view, taken partly in section, of another embodiment of the syringe of the present invention.

Another embodiment of the present invention is illustrated in FIG. 5, in which like reference numerals designate like parts. In this embodiment, the syringe barrel 12 has an enlarged section 50 at a proximal end of the barrel which has an internal diameter greater than the outer diameter of the plug 16 including the flanges 36 and 42. The plug 16 may be positioned in the section 50 for extended storage prior to use in order to minimize contact of the plug 16 against the syringe barrel 12, and thus minimize the possibility that the plug flanges may otherwise assume a set due to prolonged contact against the syringe barrel.

The foregoing detailed description is given for clearness of understanding only, and no unnecessary limitations should be understood therefrom, as modifications will be obvious to those skilled in the art.

I claim:

1. A low friction syringe, comprising:
 a barrel having an inner surface defining a chamber;
 a plunger having a distal end received in the barrel chamber; and
 a plug of elastic material received in said chamber and having a body portion secured to said distal end of the plunger, said plug having a first annular flange extending forwardly from said body portion, said first flange having an enlarged outer annular lip lightly contacting the inner surface of said barrel, and an annular hinge portion adjacent said body portion of reduced thickness relative the thickness of said lip, said plug having a second annular flange extending rerwardly from the body portion, said second flange having an enlarged outer annular lip lightly contacting the inner surface of said barrel, and an annular hinge portion adjacent said body portion of reduced thickness relative the thickness of the second flange lip, said first and second flanges defining an annular cavity intermediate the body portion and the barrel, said first flange flexing against the inner surface of the barrel responsive to a slightly greater pressure in the chamber relative the cavity during forward movement of the plunger in the barrel, and said first flange flexing about its hinge away from the inner surface of the barrel responsive to a slightly less pressure in the chamber relative the cavity and said second flange flexing against the inner surface of the barrel responsive to a slightly less pressure in the communicating chamber and cavity relative the pressure rearward the plug during rearward movement of the plunger in the barrel, said plug having a width between inner ends of said hinge portions of the first and second flanges substantially greater than the thickness of the first and second flanges, such that said plug flexes substantially only in said flange portions and the second flange contacts the barrel during said forward and rearward movements of the plunger in the barrel.

2. The syringe of claim 1 wherein said barrel and plunger are constructed from a plastic material.

3. The syringe of claim 1 wherein said barrel includes an enlarged section adjacent a rearward end of the barrel having an internal diameter slightly larger than the outer diameter of the first and second flanges.

* * * * *